US012629459B2

(12) United States Patent
Müller et al.

(10) Patent No.: US 12,629,459 B2
(45) Date of Patent: May 19, 2026

(54) SWING DEVICE FOR MOVING A BLOOD BAG AND METHOD FOR OPERATING A SWING DEVICE

(71) Applicant: Fresenius Kabi Deutschland GmbH, Bad Homburg (DE)

(72) Inventors: Marcus Müller, Ortenberg (DE); Lars Michel, Rosbach v.d. Höhe (DE); Michael Schäfer, Friedberg (DE)

(73) Assignee: Fresenius Kabi Deutschland GmbH, Bad Homburg (DE)

( * ) Notice: Subject to any disclaimer, the term of this patent is extended or adjusted under 35 U.S.C. 154(b) by 748 days.

(21) Appl. No.: 17/970,707

(22) Filed: Oct. 21, 2022

(65) Prior Publication Data

US 2023/0128153 A1 Apr. 27, 2023

(30) Foreign Application Priority Data

Oct. 25, 2021 (EP) ..................................... 21204516

(51) Int. Cl.
*A61M 1/02* (2006.01)
(52) U.S. Cl.
CPC ....... *A61M 1/025* (2013.01); *A61M 2205/103* (2013.01); *A61M 2205/3561* (2013.01); *A61M 2205/50* (2013.01)
(58) Field of Classification Search
CPC ........................ A61M 1/025; A61M 2205/103
See application file for complete search history.

(56) References Cited

U.S. PATENT DOCUMENTS

| | | | | | |
|---|---|---|---|---|---|
| 3,924,700 A | * | 12/1975 | Lindsey | ........... | A61B 5/150221 |
| | | | | | 604/245 |
| 5,057,429 A | * | 10/1991 | Watanabe | .............. | C12M 25/02 |
| | | | | | 435/297.1 |
| 5,371,329 A | * | 12/1994 | Fillaud | ................... | G01G 17/06 |
| | | | | | 177/245 |
| 2006/0013063 A1 | * | 1/2006 | Singh | .................... | B01F 35/531 |
| | | | | | 366/239 |

(Continued)

FOREIGN PATENT DOCUMENTS

| | | | | |
|---|---|---|---|---|
| CN | 214210280 U | 9/2021 | | |
| WO | WO-9504557 A1 | * | 2/1995 | ............. G01G 17/04 |
| WO | 2016084001 A1 | 6/2016 | | |

OTHER PUBLICATIONS

Extended European Search Report dated Mar. 21, 2022 issued in connection with EP Appl. 21 204 516.5.

*Primary Examiner* — Marc C Howell
(74) *Attorney, Agent, or Firm* — Cook Alex Ltd.

(57) ABSTRACT

A swing device for moving a blood bag includes a stand, a tray for receiving the blood bag, the tray being pivotable with respect to the stand, an electromotive drive device operatively coupled to the tray for causing a rocking movement of the tray with respect to the stand, and a control device for controlling operation of the drive device. The drive device includes a rotatable shaft member which is rotatable for driving the rocking movement of the tray. The drive device also includes a position encoding device configured to encode a rotary position of the rotatable shaft member of the drive device, wherein the control device is configured to determine a position of the tray with respect to the stand based on an encoder value indicative of the rotary position of the rotatable shaft member.

19 Claims, 3 Drawing Sheets

(56)                    References Cited

U.S. PATENT DOCUMENTS

| | | | | |
|---|---|---|---|---|
| 2008/0080305 | A1* | 4/2008 | Malasky | B01F 31/26 |
| | | | | 366/208 |
| 2013/0316446 | A1* | 11/2013 | Andersson | B01F 31/23 |
| | | | | 435/305.1 |

* cited by examiner

SWING DEVICE FOR MOVING A BLOOD BAG AND METHOD FOR OPERATING A SWING DEVICE

CROSS-REFERENCE TO RELATED APPLICATION

This application claims the benefit of and priority to European Patent Application No. 21204516.5 filed on Oct. 25, 2021, the disclosure of which is incorporated herein by reference in its entirety.

FIELD

The invention relates to a swing device for moving a blood bag and to a method for operating a swing device for moving a blood bag.

A swing device of this kind comprises a stand and a tray for receiving the blood bag, the tray being pivotable with respect to the stand. An electromotive drive device is operatively coupled to the tray for causing a rocking movement of the tray with respect to the stand. The drive device comprises a rotatable shaft member which is rotatable for driving said rocking movement of the tray. A control device controls operation of the drive device.

BACKGROUND

Within a blood donation process it is of significant importance to mix donated blood in a timely fashion with an anticoagulant. For this, the anticoagulant is added to blood in a blood bag, and the blood bag is moved for achieving a desired mixing of the anticoagulant with the donated blood as contained in the blood bag. A swing device serves to receive the blood bag on the tray, such that by causing a rocking movement of the tray the blood bag is moved and hence a mixing of blood as contained in the blood bag with a substance such as in particular an anticoagulant added to the blood bag may be achieved.

Within a swing device of this type it is desirous to be able to accurately determine the position of the tray with respect to the stand. A swing device may for example comprise a weighing device for weighing the blood bag, wherein the tray shall be brought into a defined, horizontal position in order to enable a weighing of the blood bag. This requires a controlled movement of the tray to enable bringing the tray into a defined position and holding the tray in that position.

In current swing devices, for this reason, the position of the tray is observed by for example using a Hall sensor which is placed on the stand and interacts with a magnet, such as a toroidal magnet, placed on the swing. The Hall sensor herein may be used to measure a magnetic field of the toroidal magnet, such that from the field measurement the position of the tray may be determined.

With current setups, during the manufacturing of the swing device significant effort needs to be spent for adjustment and calibration. Calibration herein needs to be precise in order to allow for a position estimation, requiring a cumbersome manual calibration procedure which is hardly automizable.

In addition, during operation of the device analog output signals of the Hall sensor are processed, which are subject to disturbances caused by the mechanics or by electromagnetic radiation during a donation process, making a position estimation prone to errors.

SUMMARY

It is an object of the instant invention to provide a swing device and a method for operating a swing device which in an easy and reliable manner allows for observing the position of the tray with respect to the stand, with a possibility for conducting an automatic calibration process prior to the actual operation of the device.

Accordingly, the drive device comprises a position encoding device configured to encode a rotary position of the rotatable shaft member of the drive device, wherein the control device is configured to determine a position of the tray with respect to the stand based on an encoder value indicative of the rotary position of the rotatable shaft member.

Whereas conventionally the position of a tray is observed directly e.g. by using a Hall sensor for interacting with a magnet arranged on the tray, it herein is suggested to use a position encoding device which encodes a rotary position of the rotatable shaft member of the drive device. The position encoding device hence may be integrated in the drive device and may be used to measure the position of a rotatable shaft member of the drive device, wherein from the measurement of the rotational position of the rotatable shaft member the position of the tray with respect to the stand may be derived.

The position of the tray hence is measured indirectly by observing a rotational movement of the rotatable shaft member of the drive device. According to the rotational position of the rotatable shaft member the position of the tray during a rocking movement is determined, based e.g. on a suitable calibration.

In one embodiment, the position encoding device is configured to output a signal indicative of positional increments in the rotary position of the rotatable shaft member. The control device herein is configured to determine the encoder value based on a count value of the positional increments. For example using a position encoding device employing Hall-effect sensors or Hall-effect switches, the rotary position of the rotatable shaft member may be incrementally encoded. The signal output by the position encoding device herein may for example comprise a sequence of pulses, each pulse for example indicating one revolution or a predefined fraction of a revolution of the rotatable shaft member, such that by counting pulses an incremental change in position may be determined, the number of counted pulses being output as an encoder value, from which the position of the tray with respect to the stand may be determined. The encoder value hence matches the count value of the positional increments, wherein the count may for example start from an initial reference value which is associated with a reference position of the tray.

Each positional increment of the rotatable shaft member correlates with an increment in the position of the tray, such that by counting the positional increments of the rotatable shaft member the position of the tray may be derived. The correlation of the positional increment of the rotatable shaft member and the increment in the position of the tray herein may be determined using a suitable calibration, as it shall be explained in further detail below.

The position encoding device may for example be a digital two-phase Hall-effect encoder. A digital two-phase Hall-effect encoder may for example comprise a magnet arrangement which is movable with respect to an arrangement of two Hall-effect switches. By means of the two Hall-effect switches two phase-shifted signals may be output, such that based on the phase-shifted signals positional increments may be counted and, in addition, a sense of rotation may be determined.

In one embodiment, the drive device comprises an electric drive motor comprising a rotor and a stator, the rotatable shaft member being connected to the rotor. The rotatable shaft member hence corresponds to the rotor shaft of the rotor, which during rotation of the rotor is moved with respect to the stator. A magnet arrangement of the position encoding device may for example be rotationally fixed to the rotatable shaft member, and one or multiple Hall-effect switches may be a rotationally fixed to the stator. By means of the position encoding device hence the rotary position of the rotatable shaft member may be (incrementally) determined by counting revolutions of the rotary shaft member and, from an output encoder value, the position of the tray with respect to the stand during a rocking movement may be determined.

In one embodiment, the drive device comprises a gearing operatively connected to the electric drive motor, the gearing having a drive shaft operatively coupled to the tray for driving the rocking movement of the tray. A rotational movement of the rotatable shaft member of the drive motor hence is transferred into a rotational movement of the drive shaft of the gearing, the drive shaft of the gearing being coupled to the tray such that the rotation of the drive shaft is transferred into a rocking movement of the tray.

The gearing may for example be a transmission gearing for transmitting a rotational speed of the rotatable shaft member into a reduced rotational speed of the drive shaft. For example, the rotatable shaft member of the drive motor may conduct a fixed number of revolutions—for example a number in between 50 to 150 revolutions, for example between 80 to 120 revolutions—per revolution of the drive shaft. The rotatable shaft member hence moves faster than the drive shaft. One revolution of the drive shaft herein may correspond to one cycle of the rocking movement of the tray, such that the tray performs a complete back-and-forth movement during one 360° revolution of the drive shaft.

The transmission ratio of the gearing hence determines the number of positional increments as detected by the position encoding device during one complete cycle of the tray. If the rotatable shaft member of the drive motor for example conducts 100 revolutions per full revolution of the drive shaft and hence per cycle of the rocking movement of the tray, and each positional increment as encoded using the position encoding device matches one revolution of the rotatable shaft member, 100 positional increments of the rotatable shaft member occur during one cycle of the rocking movement of the tray. The number of positional increments as encoded by the position encoding device herein determines the resolution of determining the position of the tray.

In one embodiment, the drive shaft of the gearing carries a lever element which, when rotating the drive shaft, is rotated together with the drive shaft. The lever element comprises a coupling member, for example in the shape of a pin, which engages in a longitudinal opening of a coupling arm operatively connected to the tray. When rotating the drive shaft and hence when rotating the lever element, the coupling member of the lever element moves within the longitudinal opening of the coupling arm and, in this way, causes the coupling arm and thus the tray to perform a rocking movement with respect to the stand.

The tray herein may be pivotably connected to the stand about a pivoting axis. The drive shaft in turn may be rotatable about a rotational axis which is offset to the pivoting axis of the tray.

The coupling arm extends from the tray towards the drive shaft and via the lever element and the coupling member arranged thereon is coupled to the drive shaft, such that a rotational movement of the drive shaft is transferred into a rocking, back-and-forth movement of the coupling arm and thus the tray.

During regular operation of the swing device the position of the tray is determined based on the encoder value as derived from signals output by the position encoding device. During operation, positional increments may be counted and in this way the encoder value may be determined. Based on the encoder value and its correlation to the rocking movement of the tray the momentary position of the tray may be determined.

By controlling operation of the drive device using the control device, hence, the swing device with its tray may be brought into a defined position in case for example a weighing operation or the like shall be conducted, in which the tray should be in e.g. a horizontal position in order to allow for an accurate measurement of the weight of a blood bag received on the tray. The defined position herein may be associated with a specific encoder value, such that the tray may be moved into the defined position by driving the drive device until the encoder value is reached.

The correlation in between the encoder value and the tray position may be determined in an initial calibration process prior to the regular operation of the swing device for moving a blood bag. For example, the control device may be configured to determine, in an initial calibration process prior to the operation of the swing device for moving a blood bag, at least one reference position by controlling the drive device to cause a rocking movement of the tray and by acquiring, during the rocking movement, values of a characteristic motor parameter to define the at least one reference position based on the values of the characteristic motor parameter.

During the control movement of the tray, which may take place for example over exactly one cycle of the rocking movement, also encoder values may be acquired which are correlated to the values of the characteristic motor parameter, such that a profile of the characteristic motor parameter over correlated encoder values and hence over the position of the rotatable shaft member of the drive device is obtained. By measuring the characteristic motor parameter, hence, a correlation between the rocking movement of the tray and encoder values is determined.

The characteristic motor parameter may for example be the motor current as measured by the control device during operation of the drive motor. During the calibration process, hence, the motor current is measured e.g. over one cycle of the rocking movement of the tray.

Generally, when causing a rocking movement of the tray, the characteristic motor parameter, in particular the motor current, will vary in a defined manner, the variation of the characteristic motor parameter for example resembling a sine wave. A maximum and a minimum of the profile of the characteristic motor parameter herein correspond to defined positions of the tray, for example each to a substantially horizontal position of the tray, the variation in the motor current being due to a change in a lever arm within the coupling of the gearing to the pivotable tray. Hence, by determining a minimum and/or a maximum in the profile of the values of the characteristic motor parameter, a reference position may be derived, wherein in principle only one reference position, for example according to the minimum of the profile of the characteristic motor parameter, may be determined or two reference positions may be determined, according to a minimum and a maximum in the profile of the characteristic motor parameter.

As the minimum and the maximum correspond to defined, known positions of the tray, based on the determination of a reference position an initialization of the encoder value of the position encoding device may be carried out. For example, the encoder value at the reference position (for example corresponding to the minimum in the profile of the characteristic motor parameter) may be set, in the calibration process, to a predefined initial value, for example 0. The encoder value hence indicates a count of an incremental change with respect to the initial value (for example 0). As the tray position corresponding to the initial value is known (namely the reference position) and as furthermore the change in the tray position per increment of the encoder value is known (according to the transmission ratio of the gearing and according to a locus curve describing the coupling of the drive shaft to the tray), based on the calibration the position of the tray may precisely be determined according to the encoder value.

Generally, during the calibration process, the determination of one reference position is sufficient to initialize the encoder value based on the reference position. By determining two reference positions, corresponding to e.g. a minimum and a maximum of the profile of the characteristic motor parameter, it may be checked whether the calibration has been performed correctly in that the encoder values corresponding to the reference positions are compared and are assessed based on the (known) positional difference between the reference positions. Generally, the count of positional increments between the reference positions is determined by the mechanics of the system, in particular the transmission ratio of the gearing, such that the count should correspond to the positional distance in between the reference positions. If a mismatch occurs, it can be concluded that the calibration process, namely the determination of the reference positions, has been incorrect and hence should be repeated.

The at least one reference position may be determined based on the profile of the characteristic motor parameter, in particular the motor current as measured over one cycle of the rocking movement of the tray. In another embodiment, a reference position may be determined using for example a microswitch, a photoelectric barrier or a reed sensor, which may indicate that the tray has reached a defined reference position, such that based on the output of the microswitch, the photoelectric barrier or the reed sensor an initialization of the encoder value of the position encoding device may take place.

As the calibration may take place initially by measuring the profile of the characteristic motor parameter and by correlating the profile to encoder values, the calibration may take place automatically without user input. The calibration may be controlled by the control device. As a result of the calibration the encoder value is initialized based on a reference position, such that based on the output of the position encoding device now, during actual, regular operation of the swing device, the position of the tray may be determined, and the tray may be moved into any desired position in accordance with the output of the position encoding device.

As the position encoding device observes the rotational movement of the rotatable shaft member of the drive device, the position encoding device may be integrated into the drive device, e.g. the drive motor. This makes manufacturing easy and allows for a reduction of components as well as a use of a standard drive motor with an integrated position encoding device.

As the position encoding device may provide for a digital output, signal processing may be robust and not prone to disturbances.

As the calibration may take place automatically, no cumbersome manual steps for achieving a calibration are required.

In another aspect, a method for operating a swing device for moving a blood bag comprises: moving a tray for receiving the blood bag with respect to a stand by controlling, using a control device, an electromotive drive device operatively coupled to the tray for causing a rocking movement of the tray with respect to the stand, the drive device comprising a rotatable shaft member which is rotatable for driving said rocking movement of the tray; encoding a rotary position of the rotatable shaft member of the drive device using a position encoding device of the drive device; and determining, using the control device, a position of the tray with respect to the stand based on an encoder value indicative of the rotary position of the rotatable shaft member.

The advantages and advantageous embodiments described above for the swing device equally apply also to the method, such that it shall be referred to the above in this respect.

BRIEF DESCRIPTION OF THE DRAWINGS

The idea underlying the invention shall subsequently be described in more detail with reference to the embodiments shown in the figures. Herein.

DESCRIPTION

Figure 1:
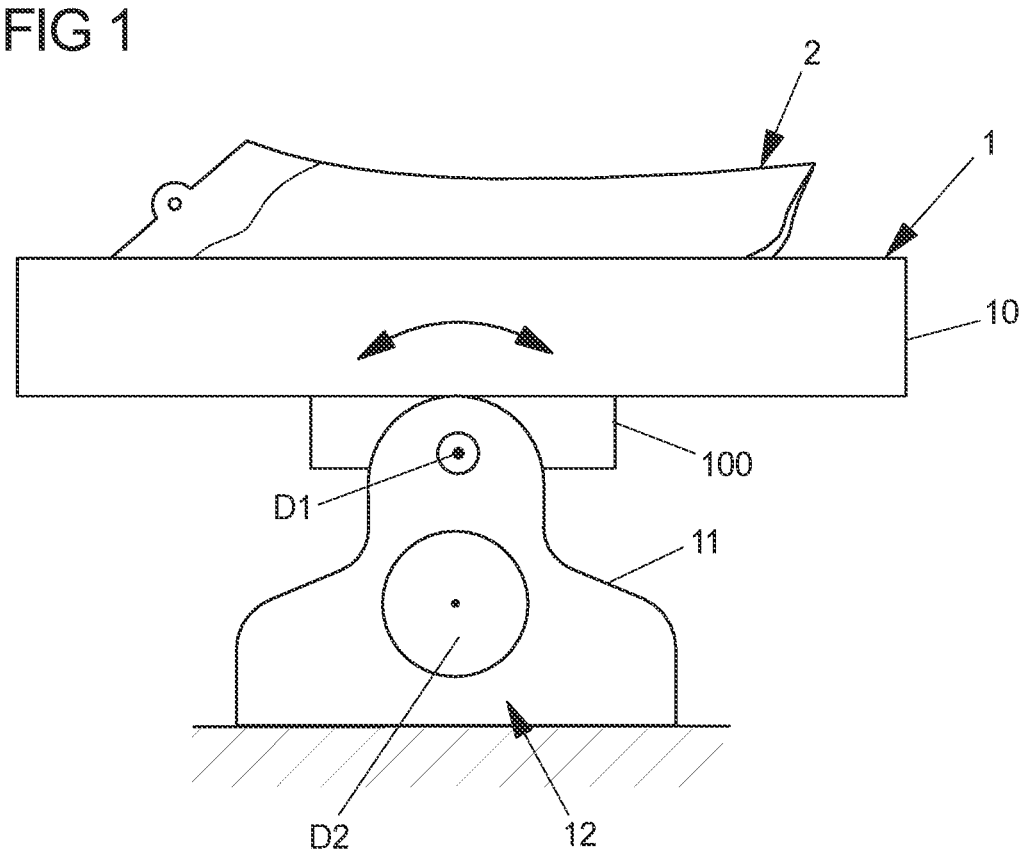
FIG. 1 shows a schematic drawing of a swing device comprising a tray for receiving a blood bag, from the front.

FIG. 1 shows, in a schematic drawing, an embodiment of a swing device 1 which comprises a tray 10 for receiving a blood bag 2.

The tray 10 is pivotably mounted to a stand 11 and is pivotably movable with respect to the stand 10 about a pivot axis D1, such that the tray 10 may perform a rocking movement with respect to the stand 11 in order to rockingly move the blood bag 2 and in this way achieve a mixing of fluid contents of the blood bag 2.

A swing device 1, as it is shown in FIG. 1, may in particular be used in connection with a blood donation process, for example a blood donation device. Blood herein is donated by a donor and is collected in a blood bag 2, wherein immediately after donation the blood shall be mixed with an anticoagulant within the blood bag 2 in order to avoid a coagulation of the blood. For this reason, the blood bag 2 with the donated blood contained therein and an added coagulant is placed on the tray 10 of the swing device 1 and, by a rocking movement, the tray 10 is gently moved to perform a mixing of the substances of the blood bag 2.

The tray 10, in one embodiment, is releasably connected to a connection member 100, which is pivotably mounted on the stand 11 about the pivot axis D1. Via the connection member 100 a connection of the tray 10 to the stand 11 is established.

Figure 2:
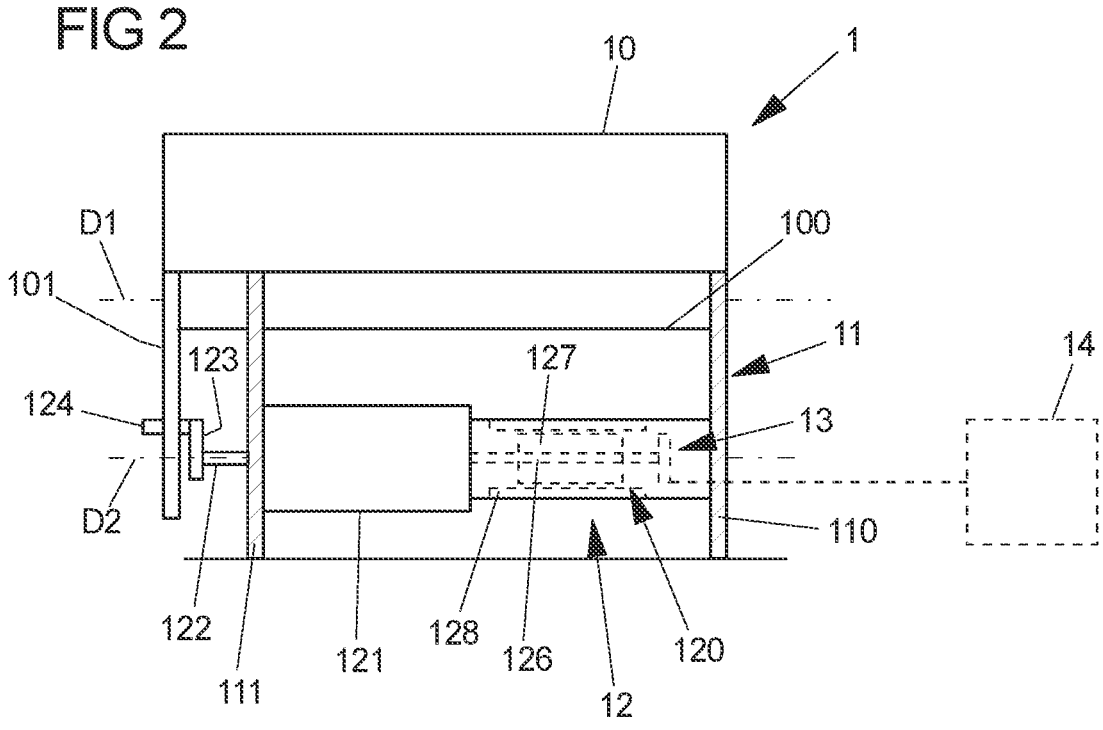
FIG. 2 shows a side view of the swing device, looking into the swing device.

The swing device 1 comprises an electromotive drive device 12 which is configured to drive the rocking movement of the tray 10. Referring now to FIG. 2, the drive device 12 comprises an electric drive motor 120 and a gearing 121. The electric drive motor 120 comprises a stator 128 and a rotor 127 arranged on a rotatable shaft member 126, the rotor 127 being rotatable with respect to the stator 128 and being electromotively driven with respect to the stator 128 during operation of the swing device 1.

The gearing 121 provides for a transmission of a rotational movement of the rotor 127 into a rotation of a drive shaft 122, wherein the gearing 121 in particular may be a reduction gearing which transmits a rotational velocity of the rotor 127 into a reduced rotational velocity of the drive shaft 122.

Figure 3:
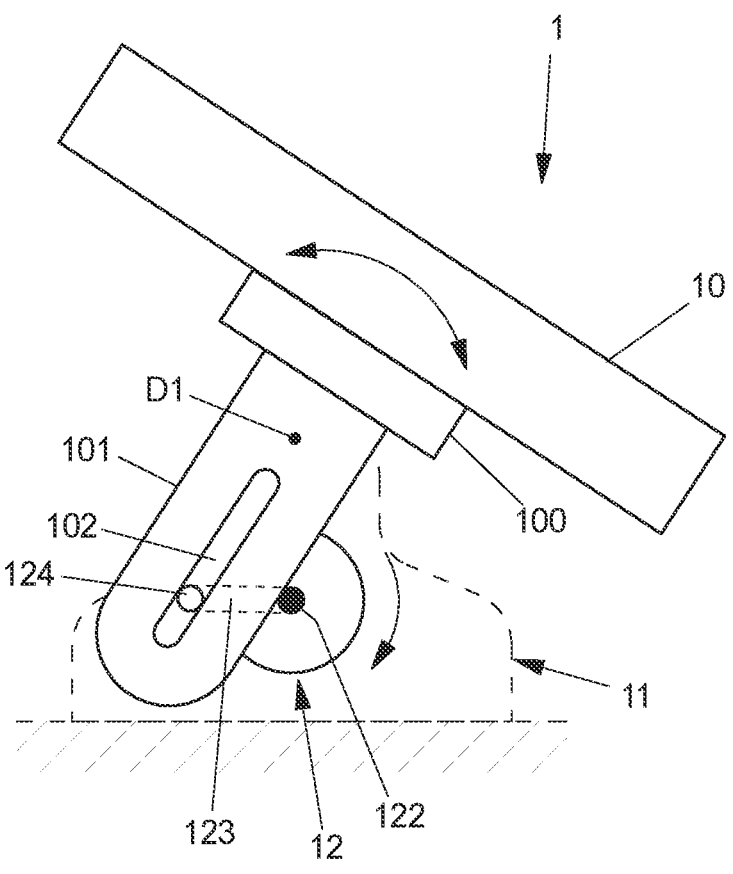
FIG. 3 shows the swing device in a tilted position of the tray.

As visible from FIG. 2 in view of FIG. 3, the drive shaft 122 carries a lever element 123 which, when rotating the drive shaft 122 about a rotational axis D2, is rotated together with the drive shaft 122. The lever element 123 carries a coupling element 124 in the shape of a pin which, when rotating the drive shaft 122, circularly moves about the rotational axis D2 and is in engagement with a longitudinal opening 102 of a coupling arm 101 fixedly connected to the connection member 100 and, via the connection member 100, to the tray 10.

By means of the coupling of the lever element 123 to the coupling arm 101 a rotational movement of the drive shaft 122 is translated into a swinging, rocking movement of the tray 10. Namely, when rotating the drive shaft 122 about the rotational axis D2 the coupling member 124 moves in the longitudinal opening 102 of the coupling arm 101 and in this way forces the coupling arm 101 and with it the tray 10 to pivot about the pivot axis D1, wherein the tray 10, during one revolution of the drive shaft 122, performs one cycle of a back-and-forth rocking movement.

The drive device 12 is controlled by a control device 14, as schematically shown in FIG. 2.

During regular operation of the swing device 1, the drive device 12 drives the tray 10 to perform a rocking movement, wherein the tray 10 continuously is set into a cyclic swinging motion and in this way moves a blood bag 2 received on the tray 10 for performing a mixing of ingredients of the blood bag 2.

In the course of operation it may be desirable to bring the tray 10 into a desired, defined position, for example into a horizontal position corresponding to the position of FIG. 1. The swing device 1, for example on the tray 10, comprises a weighing device for weighing the blood bag 2, which may be most accurate if the tray 10 is in a horizontal position, such that the weight of the blood bag 2 may be accurately measured.

Referring now again to FIG. 2, the drive device 12 comprises, integrated into the drive motor 120, a position encoding device 13 which serves to provide for a position encoding of the rotatable shaft member 126 of the drive motor 120.

Figure 5:
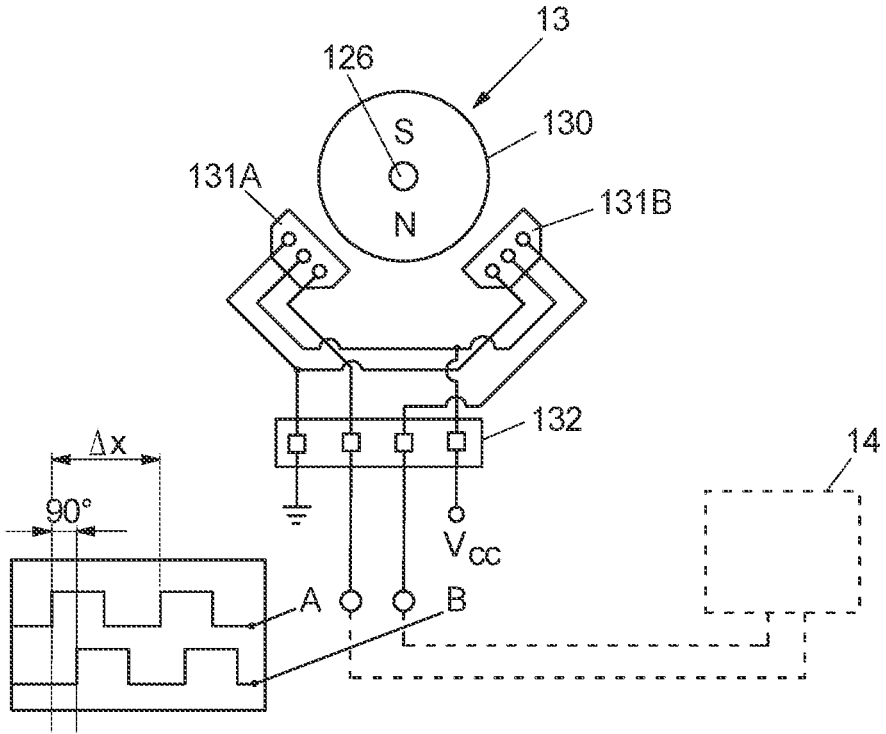
FIG. 5 shows a schematic drawing of a position encoding device used for encoding the position of a rotatable shaft member of the drive motor.

For this, as shown in an embodiment in FIG. 5, a magnet arrangement 130 of the position encoding device 13 is fixedly arranged on the rotatable shaft member 126 such that, upon rotation of the rotatable shaft member 126, the magnet arrangement 130 is moved together with the rotatable shaft member 126. The magnet arrangement 130 comprises an arrangement of magnet poles N, S, wherein the magnet arrangement 130 may comprise a single pair of magnet poles N, S forming a magnetic dipole, or multiple pairs of magnet poles N, S, for example three pairs of magnet poles N, S, arranged such that the magnet poles N, S alternate circumferentially about a rotational axis of the shaft member 126.

The position encoding device 13 furthermore comprises two Hall-effect switches 131A, 131B which output phase signals A, B and are arranged on the stator 128. The phase signals A, B are 90° out-of-phase. Each phase signal A, B herein is made up of a sequence of rectangular pulses indicating that a corresponding one of the Hall-effect switches 131A, 131B is switched on due to the passage of one of the magnet poles N, S, as it is commonly known in the art.

The position encoding device 13 in this way implements a digital two-phase Hall-effect encoder which provides phase signals A, B as output, allowing to derive positional increments ΔX in the rotary position of the shaft member 126. Namely, each positional increment ΔX as derived from a pulse period within the phase signals A, B indicates a change in position by e.g. one revolution or by a fraction of one revolution of the rotatable shaft member 126, for example ⅓ of a revolution (e.g. when three pairs of magnet poles N, S are used on the magnet arrangement 130). The two phase signals A, B herein allow to determine, in addition to the positional increments Δx, a direction of rotation.

By counting pulses and hence by counting positional increments ΔX it is possible to incrementally observe the rotary position of the rotary shaft member 126. The control device 14 herein, via an interface 132, is connected to the Hall-effect switches 131A, 131B and is configured to process the phase signals A, B for incrementally determining an encoder value indicative of the rotary position of the rotatable shaft member 126.

During regular operation the rotational change in position of the rotary shaft member 126 can be observed according to the output signals of the Hall-effect switches 131A, 131B. To determine, from the incremental change of the rotary position of the rotatable shaft member 126, the position of the tray 10 within its cyclic rocking movement, a calibration is required which may be automatically carried out in a calibration process prior to starting regular operation. The calibration herein may be performed once prior to the first start of operation, and/or repeatedly for example prior to each mixing operation for moving a blood bag 2.

For calibrating the swing device 1 to be able to determine the position of the tray 10 with respect to the stand 11, the control device 14 in a calibration process is configured to drive the drive device 12 to cause the tray 10 to be moved over one cycle of the rocking movement. During one cycle of the rocking movement the drive shaft 122 of the gearing 121 is moved by one revolution, and correspondingly the lever element 123 is rotated by 360°, hence causing the tray 10 to be moved back and forth about its pivot axis D1.

Figure 4:
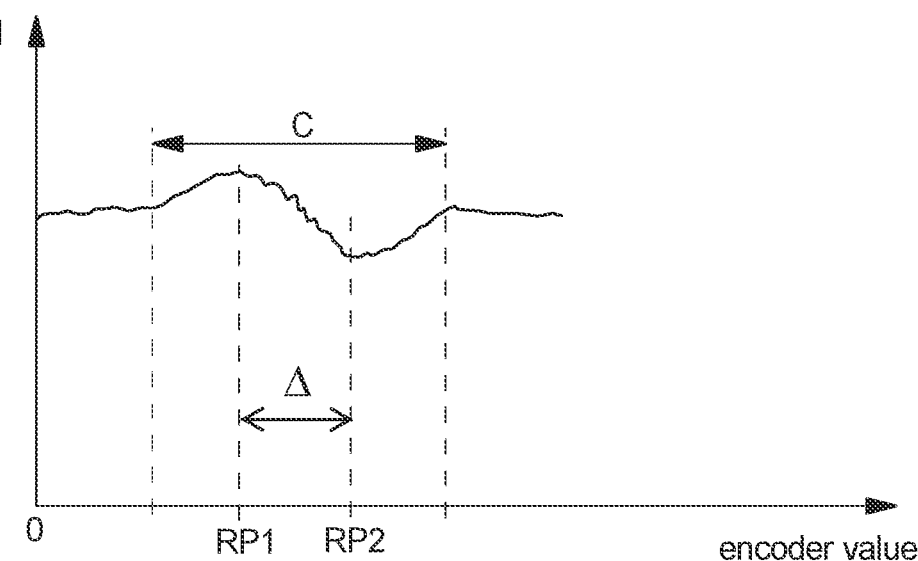
FIG. 4 shows a profile of the motor current of a drive motor of a drive device of the swing device.

During the rocking movement of the tray 10, the motor current I is measured over one cycle C of the rocking movement, as this is illustrated in FIG. 4. In addition, during the rocking movement encoder values corresponding to count values of the positional increments as derived from the signals A, B of the position encoding device 13 are acquired and stored, such that a profile of the motor current I (representing a characteristic motor parameter) over position (as indicated by the encoder values as derived from the output of the position encoding device 13) is obtained.

Within the profile of the motor current I, a maximum and a minimum are determined and are assumed to correspond to reference positions RP1, RP2. The reference positions RP1, RP2 correspond to defined positions of the tray on the cyclic path of the rocking movement. For example, the maximum and the minimum of the motor current I at reference positions RP1 and RP2 may both correspond to a horizontal position of the tray 10, the maximum current and the minimum current being caused by the change in the lever arm during rotation of the lever element 123. Hence, at the maximum and at the minimum the tray 10 can be assumed to be in its horizontal position, and hence the encoder value can be in initialized to a predefined initial value, for example 0, at either the maximum or the minimum. The encoder value hence indicates a count of positional increments with respect to the defined reference position RP1, RP2.

For fine adjustment, an offset can be added to the encoder value in order to make sure that the initialized encoder value exactly matches a predefined position, e.g. the horizontal position of the tray 10.

The reference positions RP1, RP2 (if determined correctly) are separated from one another by a fixed number of rotations of the rotatable shaft member 126 and hence by a fixed count of positional increments as detected by the position encoding device 13. This is indicated in FIG. 4 as a distance Δ, corresponding to the fixed count of positional increments between the reference positions RP1, RP2.

As the distance Δ between the reference positions RP1, RP2 (if determined correctly) is determined by the mechanics of the system, in particular the transmission ratio of the gearing 121, it can be checked by determining the actual distance Δ between the identified reference positions RP1, RP2 whether the reference positions RP1, RP2 have been identified correctly in the current profile. Namely, if the actual distance Δ substantially deviates from an expected distance as defined by the mechanics, it can be assumed that there is an error in the identification of the reference positions RP1, RP2.

Hence, based on the initialization by means of one of the reference positions RP1, RP2 the movement of the tray 10 may be controlled in that the tray 10 may be brought in a controlled manner into any position on its rocking cycle.

The transmission gearing 121 herein provides for a fixed transmission in between the output of the drive motor 120 and the drive shaft 122, for example a transmission by a transmission ratio in between 50 to 150, for example between 80 and 120, such that the rotatable shaft member 126 of the drive motor 120 moves faster by the noted transmission ratio than the drive shaft 122 and performs a number of revolutions corresponding to the transmission ratio per one revolution of the drive shaft 122. As one revolution of the drive shaft 122 corresponds to one full cycle of the rocking movement of the tray 10, the transmission ratio also indicates the number of revolutions that the rotatable shaft member 126 performs during one cycle of the rocking movement of the tray 10. According to the encoder value as initialized during the calibration routine the tray 10 hence may be brought into a controlled position using the position encoding device 13 during actual operation of the swing device 1.

The initialization of the encoder value of the position encoding device 13 may be carried out by observing a characteristic motor parameter such as the motor current I, as illustrated in FIG. 4. In another embodiment, the initialization may take place by for example using a microswitch, a photoelectric barrier or a reed sensor for detecting a reference position of the tray, for example a horizontal position of the tray, and by initializing the encoder value of the position encoding device 13 based on the detected reference position.

The idea underlying the invention is not limited to the embodiments described above, but may be implemented in an entirely different fashion.

The tray may be non-releasably coupled to the stand, or may be releasably coupled via a coupling member to the stand.

The swing device herein may be integrated into a donation device, the stand for example being implemented by a housing of the donation device.

By using a swing device as proposed herein, a calibration may be carried out automatically prior to actual operation of the swing device. A required number of components for observing a position of the tray may be reduced. Because the position encoding device is integrated in the drive device, a reliable position encoding may be achieved, with a reduced software complexity and an increase in the handling comfort for a user.

LIST OF REFERENCE NUMERALS

1 Blood bag swing device
10 Tray
100 Connection member
101 Coupling arm
102 Longitudinal opening
11 Stand
110, 111 Plate member
12 Drive device
120 Drive motor
121 Gearing
122 Drive shaft
123 Lever element
124 Coupling member (pin)
126 Rotatable shaft member
128 Stator
127 Rotor
13 Position encoding device
130 Magnet
131A, 131B Hall-effect switch
132 Interface
14 Control device
2 Blood bag
A, B Signal (phase)
C Cycle
Δx Positional increment
Δ Distance
D1 Swing axis
D2 Rotational axis
N, S Magnet pole
RP1, RP2 Reference position
Vcc Supply voltage

The invention claimed is:

1. A swing device for moving a blood bag, comprising:
a stand,
a tray for receiving the blood bag, the tray being pivotable with respect to the stand,
an electromotive drive device operatively coupled to the tray for causing a rocking movement of the tray with respect to the stand, the drive device comprising a rotatable shaft member which is rotatable for driving said rocking movement of the tray, and
a control device for controlling operation of the drive device,
wherein the drive device further comprises a position encoding device configured to encode a rotary position of the rotatable shaft member of the drive device, and
wherein the control device is configured to determine a position of the tray with respect to the stand based on an encoder value indicative of the rotary position of the rotatable shaft member.

2. The swing device according to claim 1, wherein the position encoding device is configured to output a signal indicative of positional increments in the rotary position of the rotatable shaft member, and wherein the control device is configured to determine said encoder value based on a count value of said positional increments.

3. The swing device according to claim 1, wherein the position encoding device is a digital two-phase Hall effect encoder.

4. The swing device according to claim 1, wherein the drive device comprises an electric drive motor comprising a rotor and a stator, said rotatable shaft member being connected to the rotor.

5. The swing device according to claim 4, wherein the position encoding device comprises a magnet arrangement rotationally fixed to the rotatable shaft member and at least one Hall-effect switch rotationally fixed to the stator.

6. The swing device according to claim 4, wherein the drive device comprises a gearing operatively connected to the electric drive motor, the gearing having a drive shaft operatively coupled to the tray for driving said rocking movement of the tray.

7. The swing device according to claim 6, wherein the gearing is a transmission gearing for transmitting a rotational speed of the rotatable shaft member into a reduced rotational speed of the drive shaft.

8. The swing device according to claim 6, wherein the drive shaft carries a lever element having a coupling member engaging in a longitudinal opening of a coupling arm operatively connected to the tray.

9. The swing device according to claim 1, wherein the control device is configured to determine, in a calibration process prior to operation of the swing device for moving a blood bag, at least one reference position by controlling the drive device to cause a rocking movement of the tray and by acquiring, during the rocking movement, values of a characteristic motor parameter to define said at least one reference position based on the values of the characteristic motor parameter.

10. The swing device according to claim 9, wherein the control device is configured to acquire, in the calibration process, encoder values correlated to the values of the characteristic motor parameter.

11. The swing device according to claim 9, wherein the characteristic motor parameter is the motor current.

12. The swing device according to claim 9, wherein the control device is configured to determine, in the calibration process, said at least one reference position based on a minimum and/or a maximum in a profile of the values of the characteristic motor parameter.

13. The swing device according to claim 9, wherein the control device is configured to initialize, in the calibration process, an encoder value corresponding to the at least one reference position to a pre-defined initial value.

14. A method for operating a swing device for moving a blood bag, comprising:

moving a tray for receiving the blood bag with respect to a stand by controlling, using a control device, an electromotive drive device operatively coupled to the tray for causing a rocking movement of the tray with respect to the stand, the drive device comprising a rotatable shaft member rotatable for driving said rocking movement of the tray, encoding a rotary position of the rotatable shaft member of the drive device using a position encoding device of the drive device, and determining, using the control device, a position of the tray with respect to the stand based on an encoder value indicative of the rotary position of the rotatable shaft member;

wherein the position encoding device is configured to output a signal indicative of positional increments in the rotary position of the rotatable shaft member.

15. A swing device for moving a blood bag, comprising:
a stand,
a tray for receiving the blood bag, the tray being pivotable with respect to the stand,
an electromotive drive device operatively coupled to the tray for causing a rocking movement of the tray with respect to the stand, the drive device comprising a rotatable shaft member which is rotatable for driving said rocking movement of the tray, and
a control device for controlling operation of the drive device,
wherein the drive device further comprises a position encoding device configured to encode a rotary position of the rotatable shaft member of the drive device, and wherein the control device is configured to determine a position of the tray with respect to the stand based on an encoder value indicative of the rotary position of the rotatable shaft member; and
wherein the control device is configured to determine, in a calibration process prior to operation of the swing device for moving a blood bag, at least one reference position by controlling the drive device to cause a rocking movement of the tray and by acquiring, during the rocking movement, values of a characteristic motor parameter to define said at least one reference position based on the values of the characteristic motor parameter.

16. The swing device according to claim 15, wherein the control device is configured to acquire, in the calibration process, encoder values correlated to the values of the characteristic motor parameter.

17. The swing device according to claim 15, wherein the characteristic motor parameter is the motor current.

18. The swing device according to claim 15, wherein the control device is configured to determine, in the calibration process, said at least one reference position based on a minimum and/or a maximum in a profile of the values of the characteristic motor parameter.

19. The swing device according to claim 15, wherein the control device is configured to initialize, in the calibration process, an encoder value corresponding to the at least one reference position to a pre-defined initial value.

* * * * *